US011896744B2

(12) United States Patent
Zobele et al.

(10) Patent No.: US 11,896,744 B2
(45) Date of Patent: Feb. 13, 2024

(54) CARTRIDGE WITH VAPOUR PERMEABLE MEMBRANE, IN PARTICULAR FOR VOLATILE SUBSTANCES SUCH AS INSECTICIDES AND FRAGRANCES

(71) Applicant: ZOBELE HOLDING S.P.A., Trento (IT)

(72) Inventors: Franco Zobele, Trento (IT); Walter Sordo, Trento (IT)

(73) Assignee: ZOBELE HOLDING S.P.A., Trento (IT)

( * ) Notice: Subject to any disclaimer, the term of this patent is extended or adjusted under 35 U.S.C. 154(b) by 172 days.

(21) Appl. No.: 17/225,569

(22) Filed: Apr. 8, 2021

(65) Prior Publication Data
US 2021/0228759 A1    Jul. 29, 2021

Related U.S. Application Data

(63) Continuation of application No. 15/735,015, filed as application No. PCT/IB2016/053432 on Jun. 10, 2016, now abandoned.

(30) Foreign Application Priority Data

Jun. 11, 2015    (IT) .................. 102015000022867

(51) Int. Cl.
*A61L 9/12* (2006.01)
*A01M 29/12* (2011.01)
(52) U.S. Cl.
CPC .............. *A61L 9/12* (2013.01); *A01M 29/12* (2013.01); *A61L 2209/131* (2013.01); *A61L 2209/133* (2013.01)

(58) Field of Classification Search
CPC ...... A61L 9/12; A61L 9/127; A61L 2209/131; A61L 2209/133; A01M 29/12
See application file for complete search history.

(56) References Cited

U.S. PATENT DOCUMENTS 2,615,754 A * 10/1952 Lindenberg ............ A45D 37/00
428/905
3,896,995 A *  7/1975 Lelicoff ............... A01K 27/007
43/132.1
(Continued)

FOREIGN PATENT DOCUMENTS

EP    1082969 A1 *  3/2001 ......... A47L 15/4445
EP  1 518 794 A1    3/2005
(Continued)

OTHER PUBLICATIONS

International Search Report, dated Sep. 6, 2016, from corresponding PCT/IB2016/053432 application.
U.S. Appl. No. 15/735,015, filed Dec. 8, 2017.

*Primary Examiner* — Darren W Gorman
(74) *Attorney, Agent, or Firm* — NIXON & VANDERHYE

(57) ABSTRACT

Cartridge for volatile substances in the liquid state, such as insecticides or fragrances, of the type including a tray-shaped container closed on one side with a multilayer film, said multilayer film consisting of at least one internal vapour permeable membrane and one external vapour barrier layer. Directing/assisting means are provided, adapted to direct/assist the removal of just a first portion of the external vapour barrier layer—in the form of notches, weakening lines or strengthening lines—along a desired partition line, for cartridge activation.

20 Claims, 2 Drawing Sheets

(56) References Cited

U.S. PATENT DOCUMENTS

| | | | | |
|---|---|---|---|---|
| 4,158,440 A | * | 6/1979 | Sullivan | A61L 9/12 239/6 |
| 5,164,178 A | | 11/1992 | Muysson | |
| 5,372,303 A | * | 12/1994 | Paul | A61L 9/12 239/58 |
| 5,611,486 A | * | 3/1997 | Paul | A61L 9/12 428/905 |
| 5,782,409 A | | 7/1998 | Paul | |
| 5,903,710 A | | 5/1999 | Wefler et al. | |
| 5,928,748 A | | 7/1999 | Jones et al. | |
| 5,976,503 A | * | 11/1999 | Martin | A01M 1/2077 424/45 |
| 6,012,643 A | * | 1/2000 | Barlow | A61L 9/12 206/466 |
| 6,123,935 A | * | 9/2000 | Wefler | A01M 1/2077 239/45 |
| 2003/0115834 A1 | * | 6/2003 | Kelley | A61L 11/00 53/217 |
| 2010/0308130 A1 | | 12/2010 | Gruenbacher et al. | |
| 2013/0015258 A1 | * | 1/2013 | Boyles | A61L 9/042 239/6 |
| 2014/0166774 A1 | | 6/2014 | Morhain et al. | |

FOREIGN PATENT DOCUMENTS

| | | |
|---|---|---|
| WO | 2013/014078 A1 | 1/2013 |
| WO | 2013/076033 A1 | 5/2013 |
| WO | 2014/014920 A2 | 1/2014 |
| WO | 2014/116470 A1 | 7/2014 |

\* cited by examiner

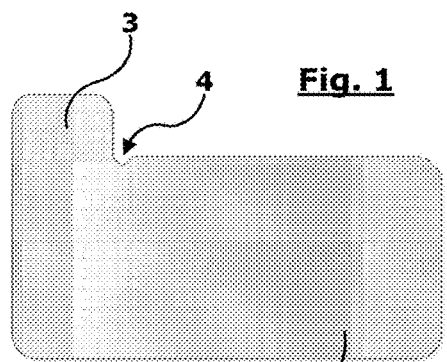
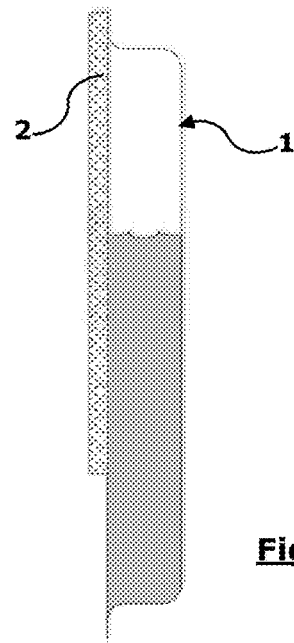
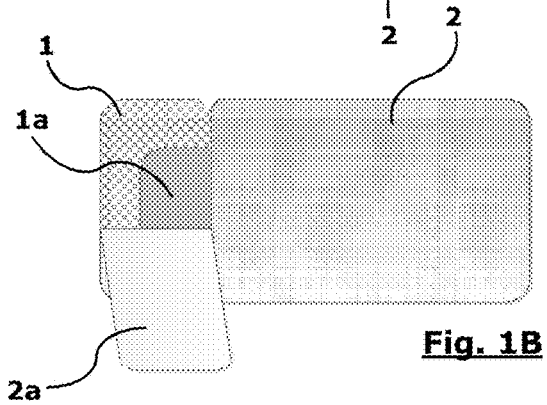
Fig. 1
Fig. 1A
Fig. 1B
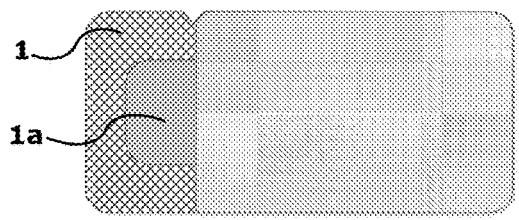
Fig. 1C
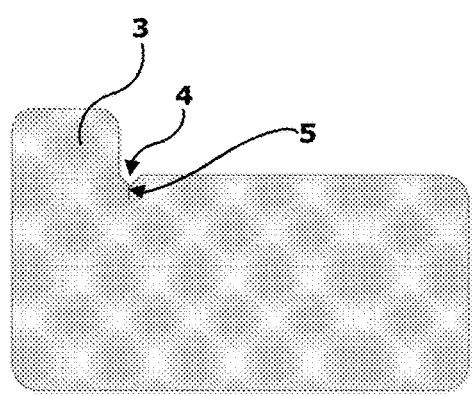
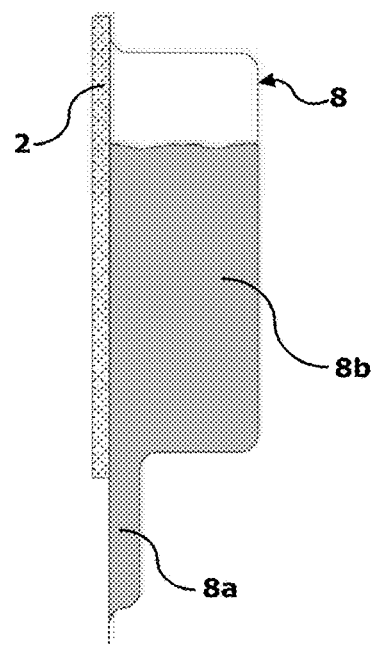
Fig. 2
Fig. 7

CARTRIDGE WITH VAPOUR PERMEABLE MEMBRANE, IN PARTICULAR FOR VOLATILE SUBSTANCES SUCH AS INSECTICIDES AND FRAGRANCES

CROSS-REFERENCE TO RELATED APPLICATION

This application is a continuation of U.S. patent application Ser. No. 15/735,015 filed on Dec. 8, 2017, which is the national phase of PCT International Application No. PCT/IB2016/053432 filed on Jun. 10, 2016, which claims priority to IT Patent Application No. 102015000022867 filed on Jun. 11, 2015, the contents of which are hereby incorporated by reference.

FIELD OF THE INVENTION

The present invention relates to a cartridge for containing volatile substances, such as liquid insecticides and fragrances, wherein at least one of its walls is closed with a vapour permeable membrane.

BACKGROUND OF THE PRIOR ART

Systems consisting of a box-shaped container, or cartridge, closed on at least one of its walls with a vapour permeable membrane, are well known in the art; they are used to make a reserve of substances which are sufficiently volatile to be able to slowly emanate outwardly through said membrane, such as certain insecticides or perfumes in liquid form.

These systems consist of a cartridge, which is often thermoformed and generally shaped as a tray with raised edges; these edges are connected to a peripheral flat flange on which a vapour permeable membrane is applied, this membrane hermetically closing the tray to substances in liquid or gel form, while permitting vapours of said substances to pass through.

These cartridges are generally used with the membrane in a vertical position, in order to achieve a slim design of the device and to allow a visual inspection of the level of the residual liquid in the cartridge.

During storage and transportation, and in any case before the device is activated, evaporation of the liquid is prevented through a vapour barrier layer, such as a thin sheet of aluminium, sealingly applied over the vapour permeable membrane. This vapour barrier layer is stuck to the membrane with per se known means, which allow its removal. To facilitate its removal, the vapour barrier layer is equipped with a projecting tab extending out of the membrane, so that said vapour barrier layer is removed by pulling said tab in a convenient tearing direction, before the first use of the cartridge by the consumer.

DRAWBACKS OF EXISTING SOLUTIONS THAT THE INVENTION IS AIMED TO SOLVE

Although the above said known devices, comprising a membrane diffuser of volatile substances, have found great success in the market, they generally have the drawback that their evaporation rate profile decreases too quickly.

Static volatile substances, i.e. air fresheners, already present the general issue that the most volatile components of the fragrance formulations evaporate first, therefore remaining, after a certain time, only the heavier ones, with a consequent decreasing intensity of evaporation and a change in the fragrance features.

Moreover, membrane cartridges have the additional technical issue that the portion of the membrane which is in contact with the liquid is able to contribute to the evaporation of the liquid to a much greater extent than the portion of the membrane which is in contact with the vapours inside the cartridge. Thus, since throughout the life of the product the liquid level gradually decreases, also the soaked surface of the membrane correspondingly decreases, and therefore the evaporation rate of the volatile substance is consequently reduced.

Some attempts have been made to design a special profile of the container, in order to reduce the decrease of the liquid level as much as possible: for example, document EP-1.518.794 discloses a cartridge which has an upper zone much wider than the lower zone. Thanks to this expedient, the decrease in the evaporation rate over time is less pronounced, but still it remains a significant difference between the evaporation rate at the beginning and at the end of use.

A constant release rate over time is just a good thing when the volatile substance is a fragrance, but it becomes an essential requirement when there is a need of delivering a precise dose of active ingredient for the volatile substance, as in case of pharmaceutical or insecticide applications. Therefore, there is a need for a container for volatile substances, which provides a more stable evaporation rate over time.

SUMMARY OF THE INVENTION

An object of the invention is therefore to propose a cartridge container for volatile liquids, provided with a membrane permeable to vapours of said liquids, which allows an evaporation rate as homogeneous and stable as possible for the entire life of the container. This object is achieved with a cartridge for liquid volatile substances, comprising a tray-shaped container closed by a multilayer film, said multilayer film consisting of at least one internal vapour permeable membrane and of an external vapour barrier layer, the cartridge comprising directing means and assisting means adapted to respectively direct and assist the removal of only a first portion of the external vapour barrier layer, according to a desired partition line, for cartridge activation, wherein said directing means comprise an opening starter of said desired partition line and wherein said assisting means comprise weakening lines positioned at the two sides of the desired partition line to assist the tearing action triggered by said opening starter. The dependent claims define preferred features of the invention.

BRIEF DESCRIPTION OF THE DRAWINGS

Further features and advantages of the invention will anyhow be more evident from the following detailed description of some preferred embodiments of the same, given as a mere and non-limiting example and illustrated in the attached drawings, wherein:

FIG. 1 is a plan view of the cartridge according to the present invention, which shows a V-notch along a longitudinal edge; FIG. 1A shows the position of use of the cartridge itself, and FIGS. 1B and 1C show the activation mode thereof, by removal of a portion of the barrier layer along a desired partition line;

FIG. 2 is a view of an embodiment variant, in which the effect of the V-notch is completed by a straight-notch at the apex of the V-notch, extending into the vapour barrier layer along said partition line;

FIG. 7 is a side view, in a vertical position of use, of an embodiment variant which has a different shape of the thermoformed body of the cartridge.

DETAILED DESCRIPTION OF THE PREFERRED EMBODIMENTS

Figure 4:
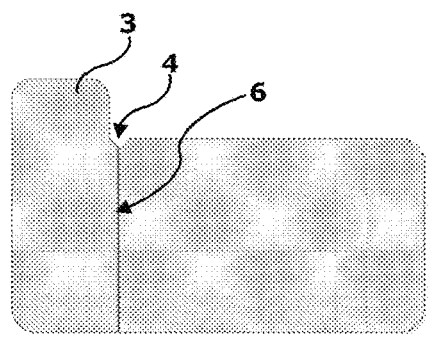
FIG. 4 is a view of an embodiment variant, similar to that shown in FIG. 2, in which the effect of the V-notch is completed by a laser-cut line, formed in correspondence of said partition line.

In its preferred embodiment, the invention consists in a container that comprises a tray-shaped body 1 and its flat closure element 2 (FIG. 1A). Hereinafter this construction is briefly referred to as "cartridge".

For ease of presentation, hereinafter, both in the description and in the attached drawings, reference will be made exclusively to an embodiment of the cartridge for volatile substances in the liquid state which is suitable for use in a natural evaporation device, as a refill. However, it must be clear that such a cartridge can also be used in assisted evaporation devices, by making simple shape adjustments within the obvious reach of a skilled man in the art, for example by means of external heating or ventilation sources.

The body 1 is preferably made by thermoforming of plastic material, with a cavity adapted to contain the volatile substance. This thermoformed body consists of the coupling between an outer layer of material having good mechanical performance—such as PET, PVC, PP or other material known for this type of applications—and an inner layer with low melting point, such as PE, adapted to allow a correct welding with the closure element 2. Moreover, an intermediate layer of additional barrier material can also be provided, so as to extend the shelf life of the product. In this sense, a preferred coupling may be a three-layer PET/EVOH/PE material in a thickness of 300 to 600 microns.

The closure element 2 consists of a multilayer film comprising:

- a lower layer, which in the assembled cartridge will be the one facing the thermoformed tray-shaped body 1, formed by the above mentioned vapour permeable membrane made of such a material that it can be welded or differently joined, in a liquid-tight manner, to the outer edge of the tray-shaped body 1;
- an upper layer, which in the assembled cartridge will be the one facing outwards, consisting of a peelable vapour barrier layer, e.g. an aluminium film;
- an intermediate release layer, which allows to maintain the mechanical coupling between the vapour permeable membrane and the vapour barrier layer, during the transport and storage steps, while the degree of adhesion provided by the release layer has however to be kept sufficiently low in order to allow the removal of the vapour barrier layer when activating the cartridge;
- an optional outer layer of plastic material, which protects the aluminium film from oxidation and improves its strength, to avoid tearing of the aluminium layer before activation.

As known, this multilayer film is manufactured independently from the tray-shaped body 1. In other words, the coupling between the aluminium film, the release layer and the membrane is performed in a separate process, which takes place before the step in which said multilayer film is welded on the edge of the thermoformed tray-shaped body 1. In the embodiment illustrated in FIGS. 1 and 1A, it can be seen that the tray-shaped body 1 has a substantially rectangular plan shape and a relatively small thickness. The closure element 2 has an outline corresponding to that of the tray 1, but in addition it has an appendix 3, formed by an extension only of the peelable vapour barrier layer of the multilayer film, which thus forms a gripping tab for the removal of the vapour barrier layer.

FIG. 1A shows the method of use of the cartridge according to the invention, which method provides for the vertical positioning of the cartridge, more specifically with the closure surface 2 lying on a vertical plane. In the same FIG. 1A it can be seen that, while the cartridge is being used, the reserve evaporable liquid obviously collects in the lower part of the cartridge, so accomplishing the function better described below.

According to a first primary feature of the present invention, the peelable vapour barrier layer is divided into two portions, along a desired partition line, and the removal of a first of said two portions, precisely the lower one in use, is carried out when the cartridge is activated, while the second portion remains permanently attached to the vapour permeable membrane.

In this way, after activation, the vapour permeable membrane remains in turn subdivided into two parts:

- an active part, which is the part where the vapour barrier layer has been removed, and therefore allows the outside evaporation of the liquid contained in the cartridge, and
- an inactive part, which is the part covered with the remaining part of the vapour barrier layer that stays adherent to the vapour permeable membrane throughout the life of the product, where no evaporation occurs.

In this way, when the cartridge of the invention is in use (FIG. 1A), the rate of evaporated liquid is exclusively related to the size of the first removed portion 2a of the vapour barrier layer and no longer to the residual liquid content. For a major part of the useful life of the device—i.e. until the liquid level inside the tray-shaped body 1 reaches the proximity of the partition line of the first portion 2a of the vapour barrier layer—the evaporation rate of the device therefore remains perfectly constant, thus fully achieving the object of the invention.

In correspondence of the set partition line that separates the two portions of the vapour barrier layer—according to another important feature of the invention—directing and assisting means are provided for directing and assisting the separation of the first portion of the vapour barrier layer of the multilayer film from the second or remaining portion, when activating the device.

In the embodiment of FIG. 1, said directing means for the separation of the first portion of the vapour barrier layer consist in a V-notch 4, formed in the edge of the tray-shaped body 1, in a position corresponding to the beginning of the desired partition line and preferably near the inner edge of the tear-off tab 3; this simple V-notch 4—which should involve the vapour barrier layer, but which, for manufacturing convenience, may also extend to the entire multilayer film and also to the edge of the tray-shaped body 1—makes up an opening starter for the tear-off of the first portion 2a of the peelable vapour barrier layer of the closure element 2.

In other words, and as it can be seen from FIGS. 1B and 1C, when the user needs to activate the cartridge, only the first portion 2a of the vapour barrier layer of the closure element 2 should be removed, thus leaving exposed only the underlying surface 1a of the vapour permeable membrane, and therefore not the entire surface of said membrane as it happens in prior art devices.

In a second embodiment, illustrated in FIG. 2, the effect of the V-notch 4 is integrated by a straight-notch 5—starting from the apex of the V-notch 4 and extending in the direction of the desired partition line—to further facilitate proper operation of the tearing of the vapour barrier layer and to obtain a correct removal of the first portion 2a of the vapour barrier layer from the second remaining portion, which stays permanently in position.

Figure 3:
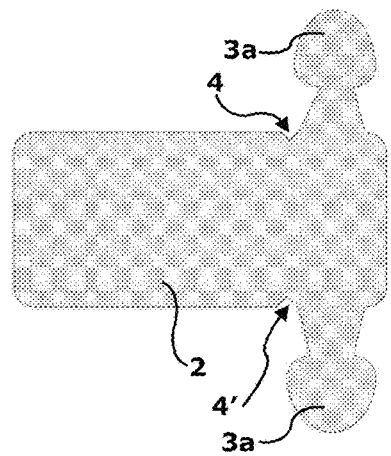
FIG. 3 is a view of a variant with two notches on opposite sides of the closure element, with two respective tear-off tabs.

In a third embodiment, illustrated in FIG. 3, two tear-off tabs 3a, 3b projecting from two opposite sides of the closure element 2 and having a shape that improves the grip by the user's fingers are provided. Immediately to the left of each of the tear-off tabs 3a, 3b, and in correspondence of the two opposite ends of the desired partition line, respective notches 4, 4' are provided. In this embodiment the tearing action thus takes place in a bilateral way and is therefore strongly directed along the desired partition line.

In a fourth embodiment, illustrated in FIG. 4, the effect of the V-notch 4 is completed by assisting means in the form of a continuous laser-cut line 6, extended in the direction of the above said straight-notch 5 up to cross the entire width of the closure element 2, and then substantially coinciding with the desired partition line. The laser-cut line 6 then allows to separate sharply said first portion 2a from the second portion of the vapour barrier layer which is intended to remain attached to the vapour permeable membrane.

Figure 5:
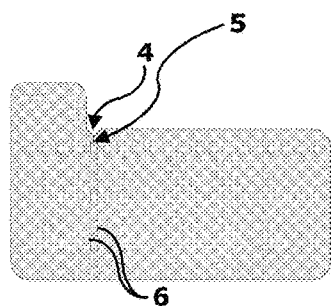
FIG. 5 is a view of an embodiment variant similar to that shown in FIG. 2 in which the effect of the V-notch is completed by two laser-cut lines arranged parallel to the two sides of said partition line.

In a fifth preferred embodiment, illustrated in FIG. 5, the effect of the V-notch 4 is completed by assisting means in the form of two continuous laser-cut lines 6, positioned at the two sides of the desired partition line and mutually parallel, by means of which the tearing action triggered by the directing means, i.e., the V-notch 4 and/or by the straight-notch 5, is then "assisted" by the two laser-cut lines 6 along the desired partition line up to the opposite part of the closure element 2.

In the various embodiments discussed above, "laser-cut" means that said cut can also be made with any other technique, such as mechanical or thermal cutting. And so also, it should be understood that the cut extends only to the vapour barrier layer without affecting the underlying vapour permeable membrane. Moreover, said cut can also consist only in a weakening groove formed on the plastic material coating layer that covers the outer face of the vapour barrier layer.

Figure 6:
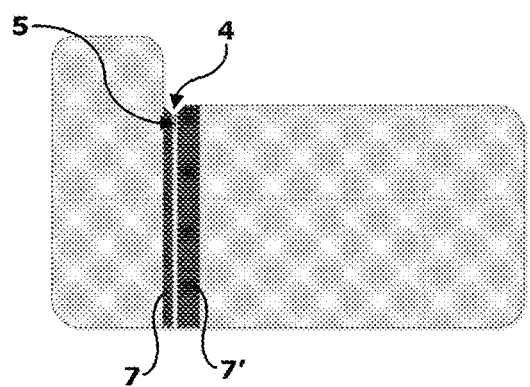
FIG. 6 is a view of an embodiment variant similar to that shown in FIG. 2 in which the effect of the V-notch is completed by two adhesive tapes arranged along the two sides of said partition line.

Another possible option, alternative to the execution of weakening lines by means of laser-cut lines, consists instead in strengthening the vapour barrier layer by applying an additional plastic protective layer, adjacent to the intended weakening lines, on one or on both sides of the desired partition line. In this sixth preferred embodiment, illustrated in FIG. 6, the effect of the V-notch 4 in directing the tearing of the first portion 2a of the peelable vapour barrier layer along a desired partition line is then assisted by two adhesive tapes 7, 7' (or by only one of them), positioned parallel to the two sides of the desired partition line, in such a way that the tearing of the vapour barrier layer is "directed" between the two additional plastic material layers.

In the above description some precise geometric directions are given for positioning the different elements which jointly form the cartridge of the present invention, among which, for example, the V-notch 4, the straight-notch 5, the laser-cut lines 6 or the adhesive tapes 7. However, it must be clear that, in the practical exploitation of the device, these different elements may also be slightly different positioned in respect of the above-mentioned geometrical definition. The scope of the invention should therefore be considered to also include a reasonable range around the positioning definitions provided here.

A further improvement that can be achieved in the cartridge of the present invention, in order to delay the moment when the liquid level coincides with the evaporation part of the membrane, is to use a tray-shaped body 1 comprising two zones having a different depth, as provided in a known manner in the above-cited document EP-1.518.794. The shallower zone will be in this case positioned in such a way as to include the whole of the above-mentioned first removable portion of the vapour barrier layer; for example, the depth of the cartridge at the lower level of the evaporation zone may advantageously be very small, i.e. about 1-2 mm, while the depth of the cartridge at the higher level, corresponding to the area where the membrane remains permanently covered by the vapour layer barrier, is significantly greater, such as 10-30 mm.

One such embodiment is shown in FIG. 7 and comprises a tray-shaped body 8, thermoformed according to a silhouette that includes a very thin lower zone 8a, which contains a minimum quantity of evaporating liquid, and a higher zone 8b which is much wider, to contain a significantly greater amount of the evaporating liquid.

As can be easily understood from the drawing, the thinner zone 8a is arranged at the portion 2a of the vapour barrier layer that is to be removed, and where, therefore, the vapour permeable membrane is active, while the zone 8b of greater depth is positioned in correspondence of the area protected by the second portion of the vapour barrier layer that is never removed.

Consequently, during use, the liquid that is located in the zone 8a defines the evaporation rate of the device, while the liquid that is located in the zone 8b, and which cannot evaporate directly, gradually replaces the liquid evaporated from the zone 8a. In this case, the evaporation rate thus remains constant practically for the entire useful life of the device.

The object of the present invention is therefore fully achieved, in a particularly simple and effective way. In fact, it is to be noted that the entire multilayer film is produced and applied to the tray-shaped body 1 with the same technologies of the known types of products while the provision of directing and/or assisting means has a totally irrelevant production cost. The cartridge according to the present invention can therefore be produced at substantially the same cost of traditional products, though having the relevant advantage of a surprisingly constant evaporation rate vs time.

It is understood, however, that the invention is not to be considered as limited by the particular arrangements illustrated above, which represent only exemplary embodiments of the same, but that different variants are possible, all within the reach of a person skilled in the art, without departing from the scope of the invention itself, as defined by the following claims.

The invention claimed is:

1. A cartridge for liquid volatile substances, the cartridge comprising:
   a tray-shaped container defining a cavity configured to contain the liquid volatile substances, the tray-shaped container being closed by a multilayer film consisting of at least one internal vapor permeable membrane and an external vapor barrier layer; and
   a directing system and an assisting system configured to respectively direct and assist removal of only a first portion of the external vapor barrier layer, according to a desired partition line, for cartridge activation, said directing system comprising an opening starter of said desired partition line, said assisting system comprising weakening lines positioned at two sides of the desired partition line to assist a tearing action triggered by said opening starter between the weakening lines and along the desired partition line.

2. The cartridge for liquid volatile substances as claimed in claim 1, wherein said opening starter comprises
   a notch formed at one end of said partition line, and
   one gripping tab extending outside said first portion in the proximity of said notch.

3. The cartridge for liquid volatile substances as claimed in claim 2, wherein said notch is a V-notch, and
   said opening starter further comprises a straight-notch formed in said vapor barrier layer starting from the V-notch and in the direction of said partition line.

4. The cartridge for liquid volatile substances as claimed in claim 1, wherein said opening starter comprises
   two notches formed at two opposite ends of said partition line, and
   two gripping tabs extending outside said first portion in the proximity of said two notches.

5. The cartridge for liquid volatile substances as claimed in claim 4, wherein said two notches are V-notches, and
   said opening starter further comprises a straight-notch formed in said vapor barrier layer starting from at least one of said V-notches and in the direction of said partition line.

6. The cartridge for liquid volatile substances as claimed in claim 1, wherein said weakening lines consist of two continuous laser-cut lines arranged parallel to the two sides of said partition line and through the entire width of said first portion of the vapor barrier layer.

7. The cartridge for liquid volatile substances as claimed in claim 1, wherein said weakening lines are obtained by applying additional plastic protective layers, arranged parallel to the two sides of said partition line and through the entire width of said first portion of the vapor barrier layer.

8. The cartridge for liquid volatile substances as claimed in claim 1, wherein said tray-shaped container comprises two different depth areas, a lesser-depth area of the two different depth areas facing said first portion of the vapor barrier layer.

9. The cartridge for liquid volatile substances as claimed in claim 2, wherein said tray-shaped container comprises two different depth areas, a lesser-depth area of the two different depth areas facing said first portion of the vapor barrier layer.

10. The cartridge for liquid volatile substances as claimed in claim 3, wherein said tray-shaped container comprises two different depth areas, a lesser-depth area of the two different depth areas facing said first portion of the vapor barrier layer.

11. The cartridge for liquid volatile substances as claimed in claim 6, wherein said tray-shaped container comprises two different depth areas, a lesser-depth area of the two different depth areas facing said first portion of the vapor barrier layer.

12. The cartridge for liquid volatile substances as claimed in claim 7, wherein said tray-shaped container comprises two different depth areas, a lesser-depth area of the two different depth areas facing said first portion of the vapor barrier layer.

13. The cartridge for liquid volatile substances as claimed in claim 1, wherein, in a normal position of use of the cartridge in which said multilayer film lies in a vertical plane, a portion of said at least one vapor permeable membrane, corresponding to said first portion of the vapor barrier layer, is permanently soaked by said liquid volatile substances for a time of a useful life of said cartridge.

14. The cartridge for liquid volatile substances as in claim 13, wherein, in said normal position of use of the cartridge, said first portion of the external vapor barrier layer corresponds to a lower portion of said multilayer film.

15. The cartridge for liquid volatile substances as claimed in claim 2, wherein, in a normal position of use of the cartridge in which said multilayer film lies in a vertical plane, a portion of said at least one vapor permeable membrane, corresponding to said first portion of the vapor barrier layer, is permanently soaked by said liquid volatile substances for a time of a useful life of said cartridge.

16. The cartridge for liquid volatile substances as claimed in claim 3, wherein, in a normal position of use of the cartridge in which said multilayer film lies in a vertical plane, a portion of said at least one vapor permeable membrane, corresponding to said first portion of the vapor barrier layer, is permanently soaked by said liquid volatile substances for a time of a useful life of said cartridge.

17. The cartridge for liquid volatile substances as claimed in claim 7, wherein, in a normal position of use of the cartridge in which said multilayer film lies in a vertical plane, a portion of said at least one vapor permeable membrane, corresponding to said first portion of the vapor barrier layer, is permanently soaked by said liquid volatile substances for a time of a useful life of said cartridge.

18. The cartridge for liquid volatile substances as claimed in claim 8, wherein, in a normal position of use of the cartridge in which said multilayer film lies in a vertical plane, a portion of said at least one vapor permeable membrane, corresponding to said first portion of the vapor barrier layer, is permanently soaked by said liquid volatile substances for a time of a useful life of said cartridge.

19. The cartridge for liquid volatile substances as claimed in claim 1, wherein the weakening lines are continuous.

20. The cartridge for liquid volatile substances as claimed in claim 1, wherein the liquid volatile substances are in a liquid state.

* * * * *